(12) United States Patent
Salomon (10) Patent No.: US 9,588,022 B2
(45) Date of Patent: Mar. 7, 2017

(54) SAMPLING DEVICE (75) Inventor: Henrik Lysgaard Salomon, Svendborg (DK)

(73) Assignee: Keofitt A/S, Svendborg (DK)

( * ) Notice: Subject to any disclaimer, the term of this patent is extended or adjusted under 35 U.S.C. 154(b) by 0 days.

(21) Appl. No.: 13/394,706

(22) PCT Filed: Sep. 13, 2010

(86) PCT No.: PCT/DK2010/050231
§ 371 (c)(1),
(2), (4) Date: May 22, 2012

(87) PCT Pub. No.: WO2011/029450
PCT Pub. Date: Mar. 17, 2011

(65) Prior Publication Data
US 2012/0227845 A1  Sep. 13, 2012

(30) Foreign Application Priority Data
Sep. 11, 2009 (DK) .................... 2009 70110

(51) Int. Cl.
*G01N 1/20* (2006.01)
*C12M 1/26* (2006.01)
*C12M 1/12* (2006.01)

(52) U.S. Cl.
CPC ........... *G01N 1/2035* (2013.01); *C12M 33/00* (2013.01); *C12M 37/00* (2013.01);
(Continued)

(58) Field of Classification Search
CPC ......... G01N 1/2035; G01N 2001/1056; G01N 2001/205; Y10T 137/86549;
(Continued)

(56) References Cited

U.S. PATENT DOCUMENTS 3,603,347 A * 9/1971 Paolini .................... 137/625.17
4,000,649 A   1/1977 Hanifl
(Continued)

FOREIGN PATENT DOCUMENTS

CN   201100853 Y   8/2008
WO    9012972 A1   11/1990
(Continued)

OTHER PUBLICATIONS

'film'. Definition [online]. Merriam-Webster Dictionary, 2013 [retrieved on Oct. 1, 2013]. Retrieved from the Internet: <URL:http://www.merriam-webster.com/dictionary/film>.*
(Continued)

*Primary Examiner* — Kevin Murphy
*Assistant Examiner* — Jonathan Waddy
(74) *Attorney, Agent, or Firm* — Sughrue Mion, PLLC (57) ABSTRACT

A sampling device including a closed sample container with a flexible wall and with an interior, a coupling member for releasable coupling to a sample outlet connector, a communicating passage between the coupling member and the interior of the sample container, at least the interior of the sample container being sterile, and a sterility protection device for ensuring the sterility of the interior of the sample container in the form of a three-way valve between the coupling member and the sample container, the three-way valve having a connection to the coupling member, a connection to the sample container and an outlet, and the three-way valve being, before use, in a closed position in which it bars access to the interior of the sample container.

14 Claims, 7 Drawing Sheets

(52) U.S. Cl.
CPC . *G01N 2001/205* (2013.01); *Y10T 137/86493* (2015.04); *Y10T 137/86549* (2015.04); *Y10T 137/86887* (2015.04); *Y10T 137/87788* (2015.04); *Y10T 137/87917* (2015.04)

(58) Field of Classification Search
CPC ..... Y10T 137/86887; Y10T 137/87788; Y10T 137/87917
USPC ............ 137/625.17, 625.46, 625.47, 625.48, 137/625.49, 861, 862, 872, 873, 874, 613; 604/19, 21, 22, 32, 33, 34, 35, 75, 164.02, 604/167.05, 171, 199, 236, 248, 323
See application file for complete search history.

(56) References Cited

U.S. PATENT DOCUMENTS

| | | | |
|---|---|---|---|
| 4,136,694 A * | 1/1979 | Kuehn | A61M 39/221 251/342 |
| 4,257,416 A * | 3/1981 | Prager | A61M 5/1408 604/250 |
| 4,423,741 A * | 1/1984 | Levy | 600/581 |
| 4,728,324 A | 3/1988 | Steigerwald et al. | |
| 4,865,583 A * | 9/1989 | Tu | A61M 39/02 604/248 |
| 5,078,688 A * | 1/1992 | Lobodzinski et al. ... | 604/167.05 |
| 5,097,840 A * | 3/1992 | Wallace et al. | 600/485 |
| 5,178,157 A * | 1/1993 | Fanlo | 600/576 |
| 5,197,968 A * | 3/1993 | Clement | A61B 17/221 604/119 |
| 5,382,240 A * | 1/1995 | Lam | 604/177 |
| 5,634,501 A * | 6/1997 | Walshe | 141/92 |
| 5,964,754 A * | 10/1999 | Osypka | 606/37 |
| 6,328,726 B1 | 12/2001 | Ishida et al. | |
| 6,544,788 B2 * | 4/2003 | Singh | 435/383 |
| 6,626,884 B1 * | 9/2003 | Dillon et al. | 604/409 |
| 6,648,006 B1 * | 11/2003 | Ostergaard | F16K 41/103 134/166 C |
| 6,730,071 B1 | 5/2004 | Dassa | |
| 6,773,673 B1 * | 8/2004 | Layfield | A61K 51/1272 422/503 |
| 7,373,825 B2 * | 5/2008 | Fennington, Jr. | 73/700 |
| 7,488,446 B2 * | 2/2009 | Meyer et al. | 422/1 |
| 7,658,201 B2 * | 2/2010 | Salomon | F16K 1/446 137/240 |
| 2003/0028156 A1 * | 2/2003 | Juliar | 604/310 |
| 2004/0078024 A1 | 4/2004 | Peluso et al. | |
| 2005/0132821 A1 | 6/2005 | Furey et al. | |
| 2007/0074761 A1 | 4/2007 | Salomon | |
| 2007/0088252 A1 | 4/2007 | Pestotnik et al. | |
| 2008/0200837 A1 * | 8/2008 | Frazier | A61B 5/1438 600/573 |

FOREIGN PATENT DOCUMENTS

| | | |
|---|---|---|
| WO | 2005040671 A1 | 5/2005 |
| WO | WO 2007/002579 A2 | 1/2007 |
| WO | 2008048511 A2 | 4/2008 |

OTHER PUBLICATIONS

Bleaching Syringes. Heroin Helper [online], Jan. 9, 2004 [retrieved on Jul. 11, 2015]. Retrieved from the Internet<URL:http://www.heroinhelper.com/user/admin/bleaching.shtml>.*
Manual for Item 26000 Aseptic System; Keofitt A/S; 2003.
Chinese Office Action dated Nov. 6, 2013, issued in corresponding Chinese Application No. 201080040210.3.
Communication dated Jul. 21, 2014 from the State Intellectual Property Office of the People's Republic of China in counterpart application No. 201080040210.3.
Communication dated Apr. 21, 2015 from the European Patent Office in counterpart application No. 10 766 237.1.
Communication dated Feb. 15, 2015 from the State Intellectual Property Office of the People's Republic of China in counterpart application No. 201080040210.3.

* cited by examiner

SAMPLING DEVICE

CROSS REFERENCE TO RELATED APPLICATIONS

This application is a National Stage of International Application No. PCT/DK2010/050231 filed on Sep. 13, 2010 which claims priority from Denmark Patent Application No. PA 2009 70110 filed Sep. 11, 2009, the contents of all of which are incorporated herein by reference in their entirety.

BACKGROUND OF THE INVENTION

Field of the Invention

The present invention relates to a sampling device. Such devices are used at, e.g., the sterile sampling through a sampling valve in a processing plant in the brewery industry, the pharmaceutical industry, the food industry, etc.

In the said industries and others, processing plants are used in which processes take place in liquids or gases, and from time to time sampling of the contents of, e.g., a container is required to monitor a process taking place in the container. In that connection, it is important that the sample is not contaminated, but that it is representative of the container contents.

Therefore, special sampling valves have been developed, see, e.g., WO9012972A and WO2005040671A. These valves are designed so that cleaning fluid, e.g., steam, may be passed through their valve housing and out through a sample outlet to clean and/or sterilize the path of a sample from the container and out through the valve.

At times, a simple cleaned, cup-shaped container is used to collect a sample which is passed out through the sampling valve when it is opened. In that way, however, there is a risk of airborne contamination of the sample so that, when analysed later, it is not representative of the contents of the container.

Therefore, a sampling device has been developed, which is marketed by Keofitt A/S under the designation: "Item 26000, Aseptic sampling system". It is in the form of a glass bottle provided with a plug containing a pre-chamber, an inlet connector, a valve which opens and closes a passage to the interior of the bottle, and a valve which opens and closes a passage to the surroundings, and a vent opening arranged between the interior and the surroundings of the bottle and provided with a filter to prevent the ingress of airborne micro-organisms. The valve which opens and closes a passage to the surroundings allows the inlet connector of the sampling device to be connected to a sample outlet connector of a sampling valve by means of a tube, whereupon cleaning fluid, such as steam, is passed through the sampling valve, the tube and the pre-chamber in the plug so that the path of the sample is cleaned and/or sterilized all the way to the chamber in the plug before sampling. However, the use of a glass bottle for sampling may involve various disadvantages. Thus, sampling in some cases takes place in a processing environment rather than in a laboratory, and glass may be a potential danger to the product and the staff. Moreover, a glass bottle system requires prior maintenance, separation, cleaning, assembly and autoclaving as the products are costly and reusable. The preparations imply an implicit user-dependent risk as concerns the sterile interior of the sample container.

BRIEF SUMMARY OF THE INVENTION

The object of the invention is therefore to provide an alternative sampling device that may ensure sterile sampling without the use of a glass bottle.

According to the invention, this is obtained by means of a sampling device which is characterized in comprising a closed sample container with a flexible wall and with an interior, a coupling member, such as a socket, for coupling to a sample outlet connector, and a communicating passage between the coupling member and the interior of the sample container, at least the interior of the sample container being sterile, and in comprising a sterility protection for ensuring the sterility of the interior of the sample container in the form of a three-way valve between the coupling member and the sample container, that is, a valve with at least three ways into and/or out of the valve, the three-way valve having a connection to the coupling member, a connection to the sample container and an outlet, and the three-way valve being, before use, in a closed position in which it bars access to the interior of the sample container. In addition to obviating glass, the use of a sample container with a flexible wall obviates the need for a vent opening as the sample container can expand as it is being filled with a sample. The sterility protection ensures that the interior of the sample container is kept sterile until the sample is collected, when it will be necessary to break the sterility protection to allow the sample to enter the sample container. By barring access to the interior of the sample container, the three-way valve closes the sample container. The sterility protection comprises or is constituted by the three-way valve, which prevents the ingress of contamination, such as airborne micro-organisms, into the sample container in its closed position. The three-way valve allows sterilization of the connection between a sampling valve and the sampling device up to the three-way valve.

In a preferred embodiment, the sampling device is a single-use product, whereby sterility may be ensured already by the manufacturer of the product.

Preferably, the three-way valve is provided with a tamper-evident blocking device. The tamper-evident blocking device ensures that the valve is not opened until the sampling device is to be used or that a user is warned if the valve has been opened so that sterility has been compromised.

The sampling device preferably comprises a temperature indicator, whereby it may be ascertained when the sterilization temperature has been reached if, e.g., steam is used for sterilization.

The outlet of the three-way valve may be provided with an outlet connector. This makes it possible to mount a pressure valve which only opens for passage when a certain pressure is present in the three-way valve, whereby it is possible to obtain a higher temperature of steam used for sterilization of the sampling valve and the connection to the sampling device.

In that connection, it should be understood that the sampling device is preferably steam sterilizable as it is preferably made from materials, at least from the coupling member to the three-way valve, both included, which can tolerate steam sterilization at the pressures and temperatures used in the relevant processing plant, e.g., 1 bar(g), 121° C., cf. www.ehedg.org.

In a preferred embodiment, the three-way valve comprises a valve housing and a movable valve body with at least one through passage. This allows the valve to be designed with few components for the sake of the manufacturing costs.

The tamper-evident blocking device preferably comprises a tear-off member preventing the three-way valve from being set to any position other than the closed position.

In one embodiment, the tear-off member comprises a member, particularly a film member, which encapsulates the three-way valve at least partially. The film member may be a substantially non-stretchable shrink film.

In a preferred embodiment, the tear-off member comprises a portion of the valve housing, which portion blocks movement of the valve body.

In an alternative or supplementary embodiment, the sterility protection comprises a sterile packaging encapsulating the sample container, the coupling member and the communicating passage between them.

Preferably, the communicating passage between the coupling member and the interior of the sample container has an internal diameter of at least 4 mm. This allows sampling of viscous liquids or liquids with suspended particles.

BRIEF DESCRIPTION OF THE SEVERAL VIEWS OF THE DRAWINGS

The invention will now be described in more detail below by means of examples of embodiments and with reference to the schematic drawing, in which.

DETAILED DESCRIPTION OF THE INVENTION

Figure 1:
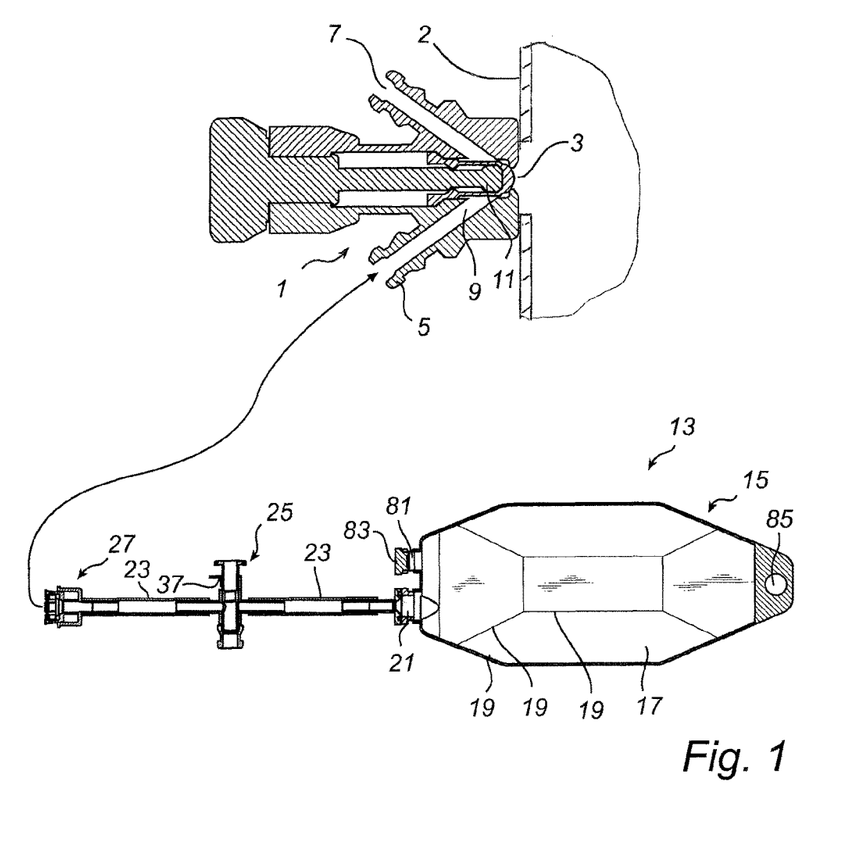
FIG. 1 is a view of a sampling valve and a sampling device according to the invention.

FIG. 1 shows a sampling valve 1 which is mounted on a wall of a container or contents container 2 to enable sampling of the contents of the contents container 2 through a sample inlet 3 in the sampling valve 1. This further has a sample outlet connector 5, a cleaning inlet 7, a valve chamber 9 and a valve body 11. The sampling valve shown otherwise substantially corresponds to the embodiment disclosed in WO9012972A. It should be understood that there is free passage through the valve chamber 9 from the cleaning inlet 7 to the sample outlet connector 5 around the valve body 11, also when the valve body 11 closes the sample inlet 3, as shown in FIG. 1.

FIG. 1 further shows a sampling device 13 comprising a sample container 15 with a flexible wall 17 made of a suitable plastics material. The wall 17 is divided into panels interconnected through welds and/or scoring lines 19 which facilitate the mutual movement of the relatively rigid panels between a flat (not shown) and an unfolded state of the sample container 15. The sample container 15 is hermetically sealed apart from an opening 21 to which a tube section 23 has been fitted. A three-way valve 25 has been inserted into the tube section 23, and at the end of the tube section 23 a coupling member in the form of a socket 27 has been provided for connection to the sample outlet connector 5 of the sampling valve 1. In this way, a communicating passage has been provided through the socket 27, the tube section 23, the three-way valve 25 in its open position to be described in detail below, and the opening 21 to the interior of the sample container 15. This communicating passage is designed so that it has an internal diameter of at least 4 mm, preferably 6 mm, throughout its course to allow the sampling of viscous liquids or liquids with suspended particles without any risk of blocking of the communicating passage.

In the embodiment shown in FIGS. 1-8, the three-way valve 23 comprises a cylindrical, tubular valve housing 29, through which extends a cylindrical valve body 31. The valve housing 29 has two opposite tube connections 33a and 33b opening into the interior of the valve housing 29. At one end of the valve housing 29 a recess 35 is provided with a shallow part 35a and a deep part 35b which is partially filled by a tamper-evident blocking device in the form of a tear-off portion 37 with a tab 39. The tear-off portion 37 is connected with the rest of the valve housing 29 through two weakened, linear areas 40.

Figure 2:
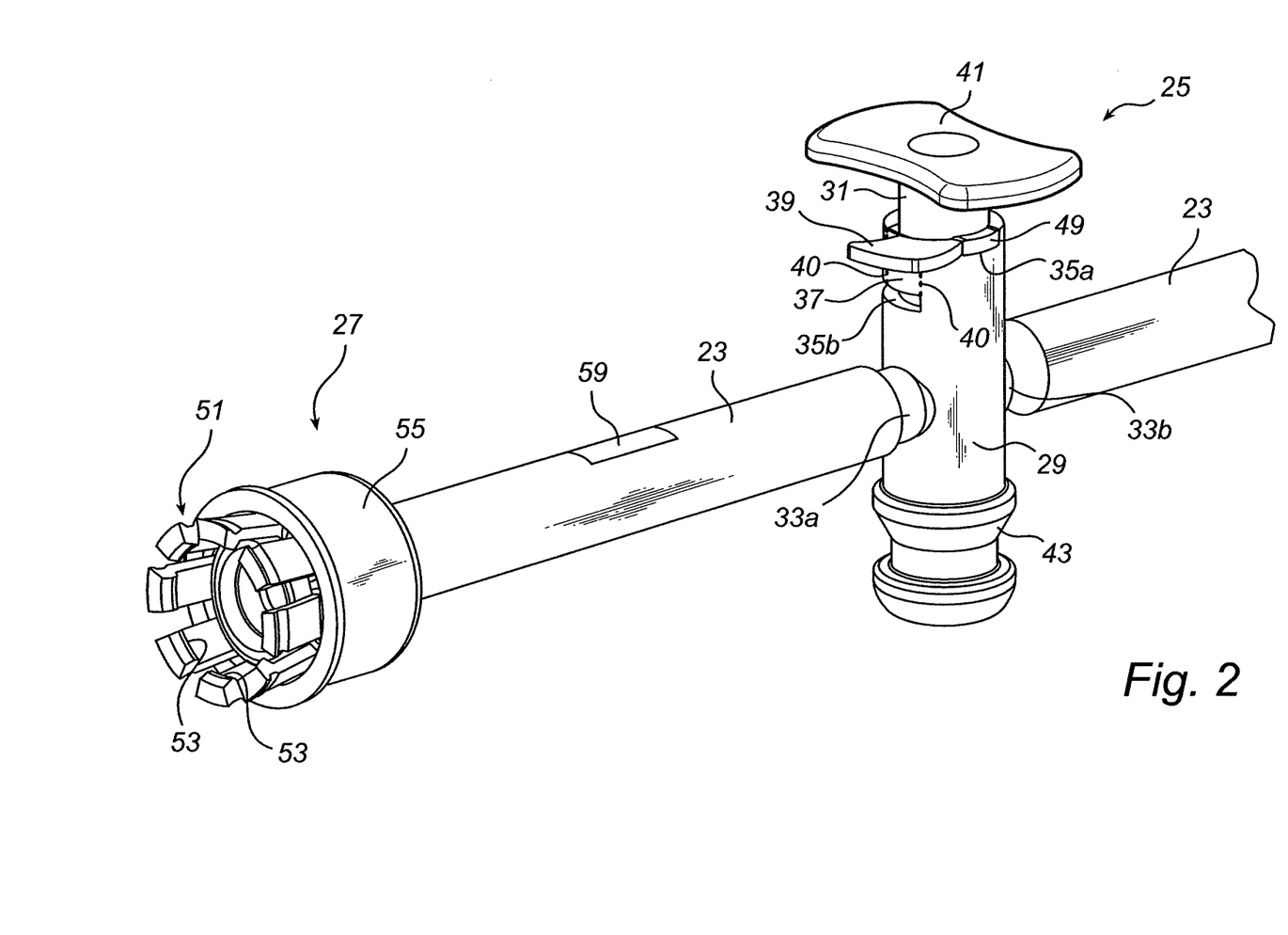
FIG. 2 is a close-up perspective view of a coupling member and a three-way valve of the sampling device of in FIG. 1.

The valve body 31 has a handle 41 at one end and is provided at the other end with a connector 43 abutting the adjacent end of the valve housing 29. The valve body 31 is tubular with an internal cavity interrupted at the middle of the length of the valve body by a transverse passage 45 which is closed against the cavity. Additionally, the valve body 31 has an opening 47 in its side through which opening 47 there is a passage out through the connector 43. Moreover, the valve body has a projection 49 located at the shallow part 35a of the recess 35 in the valve housing 29 (FIG. 2). Accordingly, the valve body 31 is in a closed position in which the passage to the interior of the sample container 15 is barred so that the sample container 15 is hermetically sealed. By contrast, at this position of the valve body 31 there is a passage in through the socket 27, the tube section 23 connected thereto, the tube connection 33a, the opening 47 in the side of the valve body 31 and out through the connector 43.

In the embodiment shown, the socket 27 is designed as a snap coupling having an internal, slotted, cup-shaped part 51 with internal claws 53 for engagement with an annular groove in a connector, such as the sample outlet connector 5, and having an outer, displaceable, cup-shaped part 55 for sliding forward over the internal cup-shaped part 51 in order to lock the claws into engagement with the connector. The bottom of the internal cup-shaped part 51 is adapted for close engagement with the connector when the claws are in engagement with the groove of the connector. In an alternative embodiment, the socket or the coupling member could be constituted by a suitably flexible, possibly widened tube end.

Figure 3:
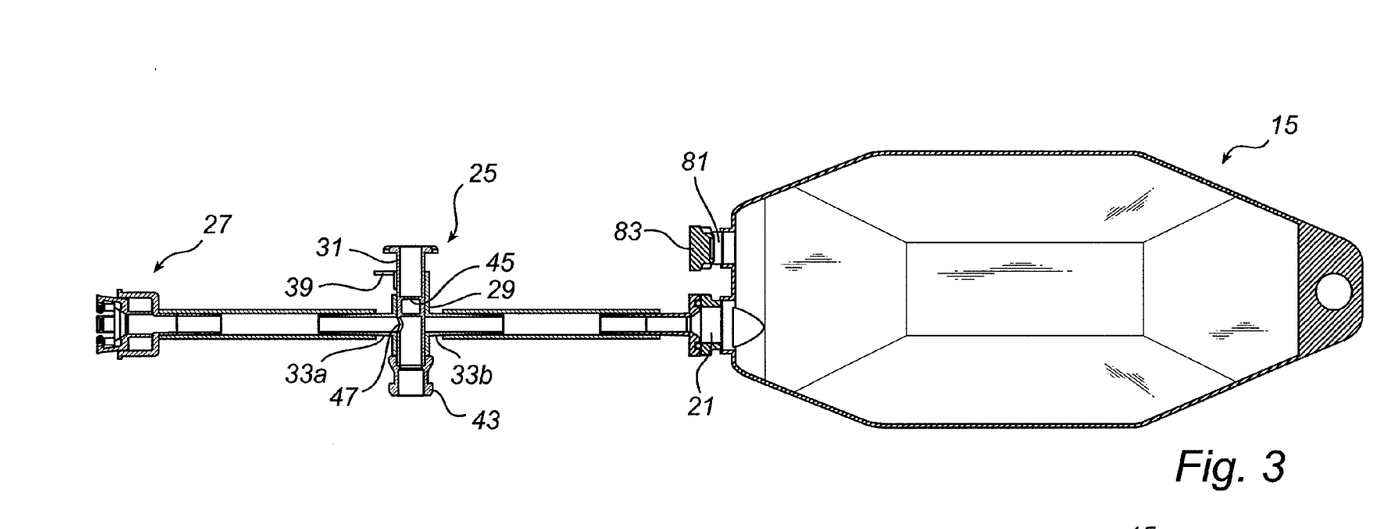
FIG. 3 is a partially sectional view of the sampling device of FIG. 1.

As shown in FIG. 3 and explained above, the three-way valve 25 is in a position in which the sample container 15 is hermetically sealed. As the sample container 15 has been sterilized, e.g. by radiation sterilization, and as it cannot be opened due to the presence of the tear-off portion 37, the sterility of the interior of the sample container 15 and the passage to the three-way valve 25 is ensured, and the tear-off portion 37 constitutes a sterility protection.

Figure 4:
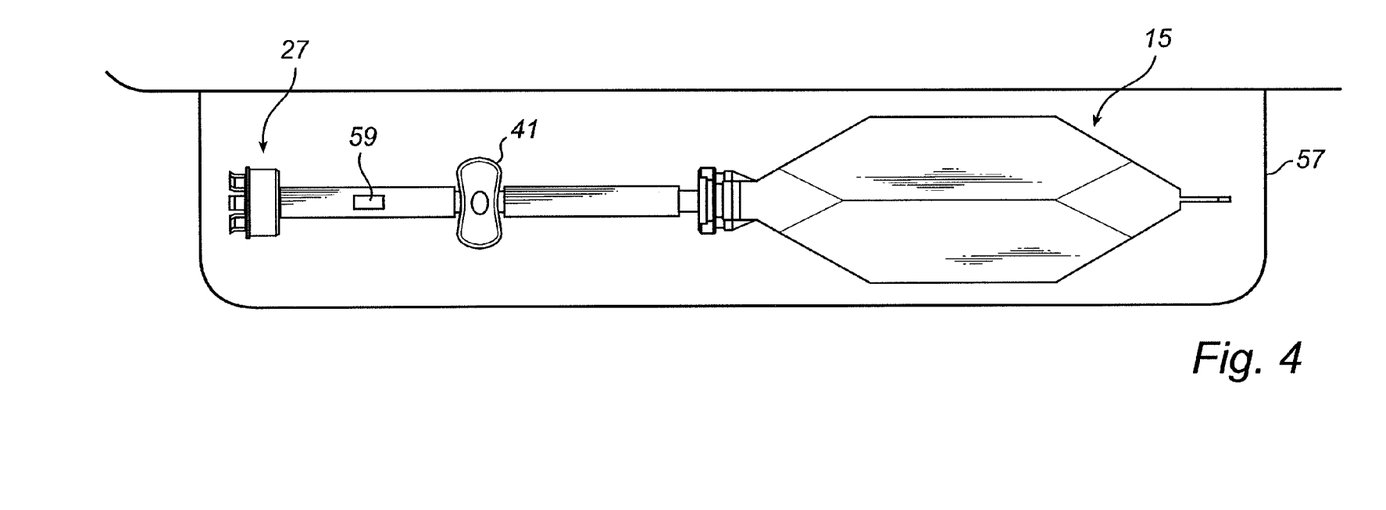
FIG. 4 is a view of the sampling device in a packaging.
Figure 5:
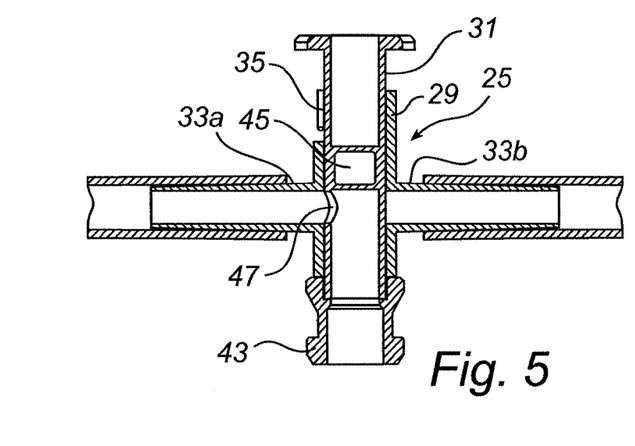
FIGS. 5-8 are sectional views of the three-way valve of FIG. 2 in different positions.

FIG. 4 shows a variant of the sampling device in which the three-way valve 25 lacks the tear-off portion 37 as compared with the embodiment of FIGS. 2 and 3. The three-way valve is in the closed position shown in FIGS. 2 and 3, but the sample container 15 with the tube section 23, the three-way valve 25 and the socket 27 is encapsulated in a sealed, sterilized packaging 57 of a type known per se to ensure the sterility of the interior of the sample container 15. In this case, the packaging 57 constitutes a sterility protection. It should be understood that, for the sake of illustration, the sample container 15 in FIG. 4 is shown in its unfolded state. In reality, the sample container 15 will be in its flat state in the packaging 57.

The sampling device is used in the following manner:

The sterilized packaging 57 is opened and removed if present. The socket 27 is connected with the sample outlet connector 5 of the sampling valve 1. Then the sampling valve is cleaned and/or sterilized in the usual manner by cleaning fluid, such as steam, being passed through the cleaning inlet 7. The cleaning fluid flows through the valve chamber 9 and out through the sample outlet connector 5. As the socket 27 is connected with the sample outlet connector 5, the cleaning fluid flows on through the tube section 23 between the socket 27 and the three-way valve 25, which is in its closed position at this point as described above. Therefore, the cleaning fluid flows in through the tube connection 33*a*, through the opening 47 in the cylindrical valve body 31 and out through the connector 43. As the three-way valve 25 is in its closed position while any packaging is removed and the socket 27 is connected to the sample outlet connector 5, the sample container 15 is prevented, due to elasticity, from unfolding and sucking in air from the surroundings, which might compromise the sterility of the interior of the sample container 15.

The connector 43 may be connected to a device for collecting the outflowing cleaning fluid and/or a pressure valve which only opens for throughflow when a certain pressure has been obtained upstream of the pressure valve so that, e.g., a higher steam pressure and thereby a higher temperature can be obtained in the parts through which the cleaning fluid or the steam flows.

In this way, the sampling valve 1 and the passage from it to the three-way valve 25 has been cleaned and/or sterilized. In the embodiment shown, a temperature indicator 59 of a type known per se indicating when a specific temperature has been reached and sterility is ensured has been provided on the tube section 23 between the socket 27 and the three-way valve 25.

The three-way valve 25 is now opened by initially removing the tear-off portion 37 if it is present. The three-way valve 25 is thus in the position shown in FIG. 5.

Figure 6:
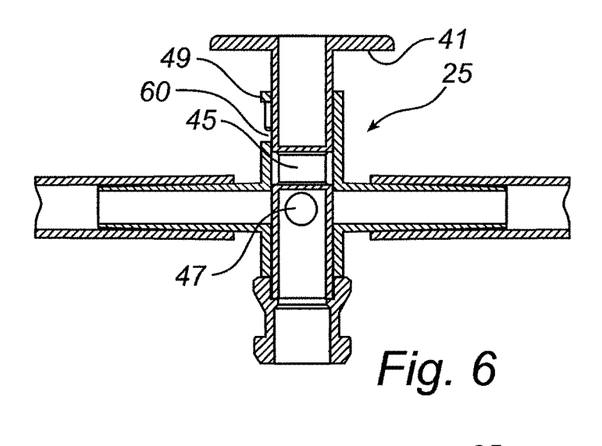

By means of the handle 41, the cylindrical valve body 31 is turned 90° to the position shown in FIG. 6, whereby the passage from the tube connection 33*a* to the connector 43 is closed, and the projection 49 is brought from the shallow part 35*a* of the recess 35 to the deep part 35*b*.

Figure 7:
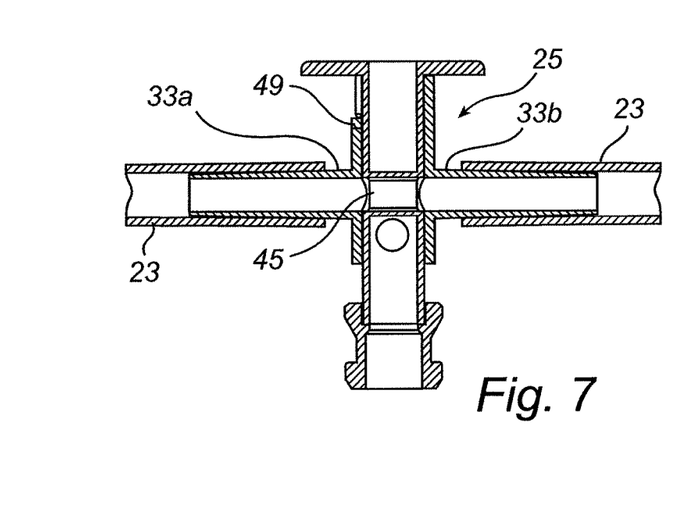

The cylindrical valve body 31 is now pressed down to the position shown in FIG. 7, the projection 49 being moved to the bottom of the deep part 35*b* of the recess 35, and the transverse passage 45 being brought into alignment with the tube connections 33*a* and 33*b*. There is now an open passage throughout the tube 23 and thereby from the sampling valve 1 to the interior of the sample container 15.

Figure 1A:
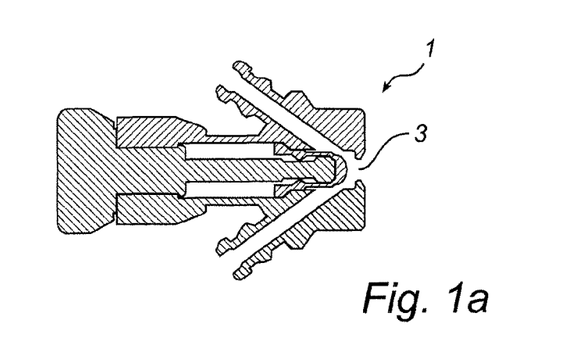
FIG. 1a is a view of the sampling valve in its open position.

The sampling valve 1 is opened in a manner known per se by the valve body 11 being moved away from the sample inlet 3 to the position shown in FIG. 1*a*, and a desired quantity of the contents of the contents container 2 is collected into the sample container 15, which expands by virtue of its flexibility as it is being filled, whereupon the valve body 11 is returned to the position shown in FIG. 1.

Figure 8:
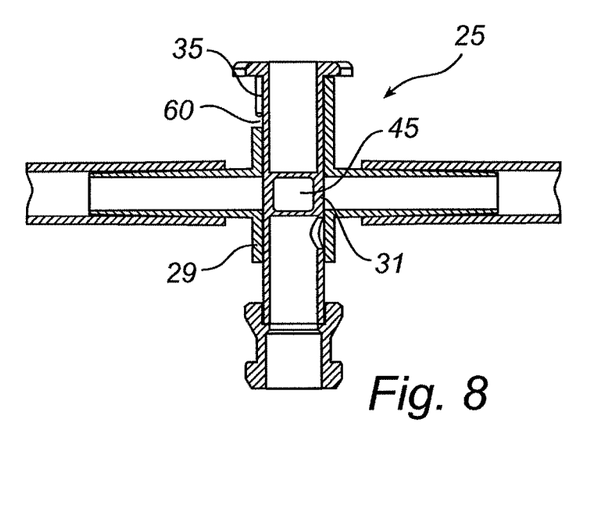

As the projection 49 slides into a groove 60 extending in the circumferential direction from the bottom of the deep end 35*b* of the recess 35, the cylindrical valve body 31 is subsequently turned a further 90° to the position shown in FIG. 8, whereby all passages in the three-way valve 25 are closed. The socket 27 can now be disconnected from the sample outlet connector 5, and the sample container 15 with sample can be taken to the laboratory for analysis of the sample without any risk of it being contaminated along the way.

Figure 9:
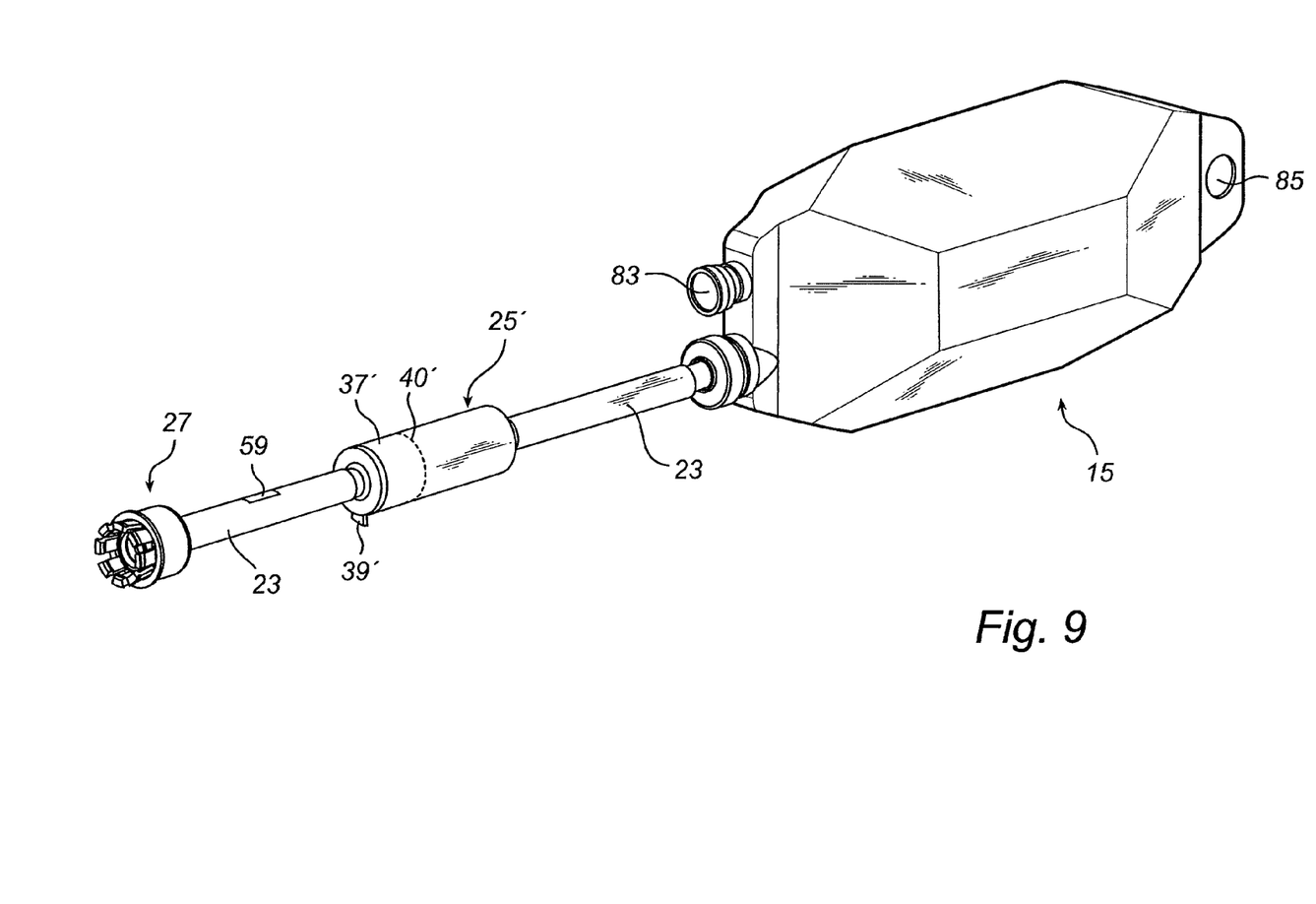
FIG. 9 is a view of a sampling device with a second embodiment of the three-way valve.
Figure 10:
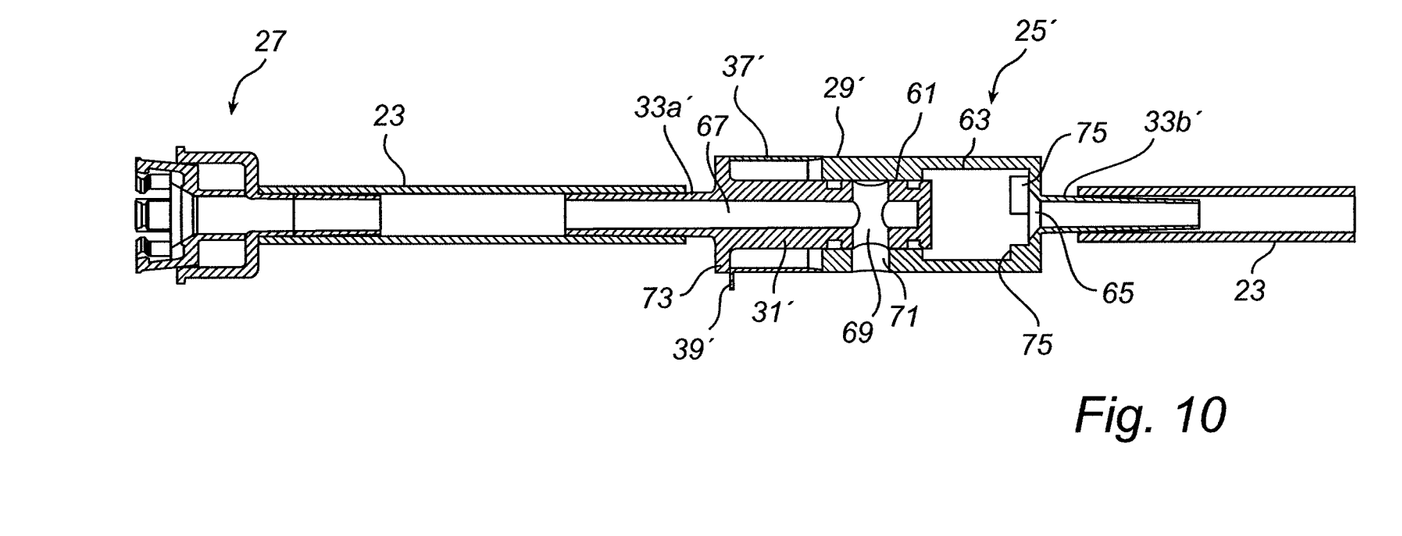
FIGS. 10 and 11 are sectional views of the second embodiment of the three-way valve in different positions.
Figure 11:
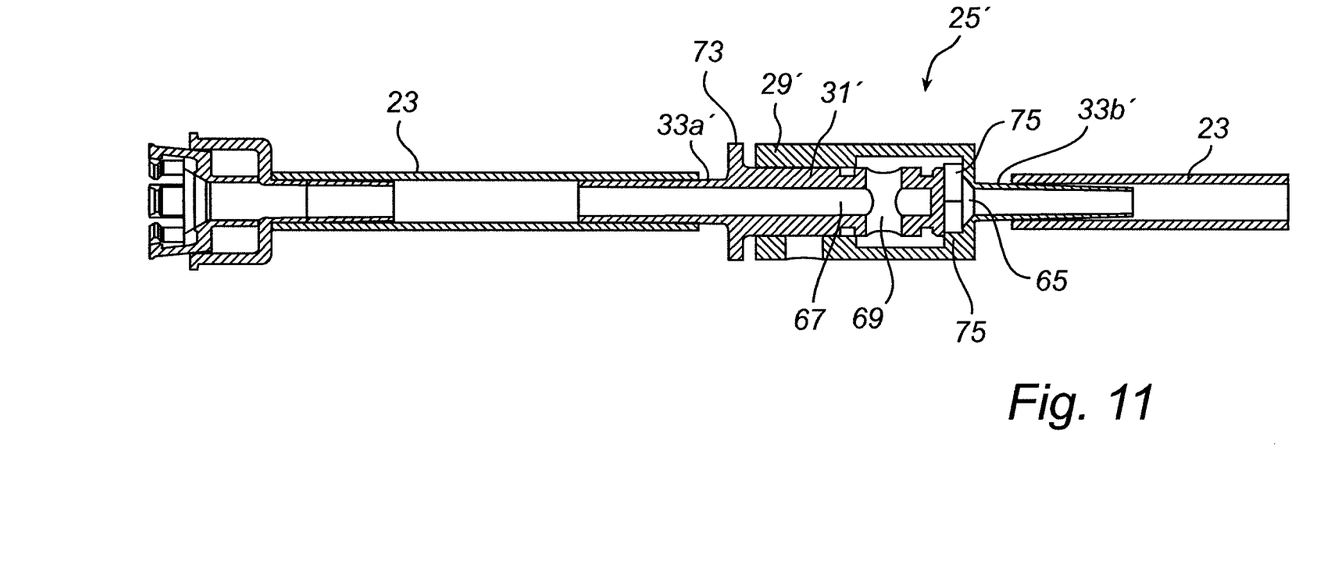

FIGS. 9-11 illustrate a sampling device 13' as the one shown in FIGS. 1 and 3, and therefore corresponding parts are provided with the same reference numerals, but with a different three-way valve 25'. This comprises an elongated valve housing 29' with an axial direction and a chamber having a first coaxial, cylindrical section 61 and a second section 63 enlarged in relation thereto. An outlet opening 65 and a tube connection 33*b*' are provided in an end wall of the valve housing 29'. A valve body 31' is axially displaceable in the valve housing 29' and has a coaxial tube connection 33*a*' and a coaxial pocket hole 67 communicating with a transverse passage 69 in the valve body 31'. The valve body 31' is sealed relative to the first coaxial, cylindrical section 61 of the chamber of the valve housing 29', and it is axially movable between a closed position shown in FIG. 10 and an open position shown in FIG. 11.

An outlet opening 71 flushing with the transverse passage 69 when the valve body 31' is in the closed position is provided in the wall of the valve housing 29'. This makes it possible to clean and/or sterilize a passage through the socket 27 and the tube section 23 up to the three-way valve 25' as described with reference to FIGS. 1-8 and particularly FIG. 5.

The valve body 31' has an annular collar 73 abutting a tamper-evident blocking device in the form of a tear-off portion 37' with a tab 39'. The tear-off portion 37' is connected with the rest of the valve housing 29' through a weakened linear area 40' and prevents the valve body 31' from being moved away from the closed position, and it thereby ensures the sterility of the sample container 15 in the same way as the tear-off portion 37 in the embodiment described above.

When the tear-off portion 37' has been removed, the valve body 31' may pressed axially in a direction towards the outlet opening 65, projections 75 in the enlarged section 63 of the valve chamber preventing the valve body from blocking the outlet opening 65. Accordingly, the three-way valve 25' is in an open position corresponding to the open position of the three-way valve 25 shown in FIG. 7 as there is a passage from the tube connection 33*a*' to the tube connection 33*b*' through the pocket hole 67, the transverse passage 69, the enlarged section 63 of the chamber of the valve housing 29', between the projections 75 and through the outlet opening 65.

It should be noted generally that the sample container is provided with a second opening 81 which is closed with a screw plug 83. This second opening 81 may possibly be used to drain off the contents of the sample container after sampling. The sample container may also be provided with a septum (not shown) for removal of part of its contents by means of a syringe. Moreover, the sample container is provided with an eye 85 which permits suspension of the sample container 15.

It should be noted that features described in connection with one embodiment may be used in several cases as a supplement or an alternative in others of the embodiments described. A non-stretchable shrink film may be used as a tamper-evident blocking device at the three-way valves 25 and 25'.

The invention claimed is:

1. A sampling device for sampling through a sampling valve attached to a contents container used in an industrial processing plant and through a sample outlet connector attached to said sampling valve downstream of said sampling valve, a sample representative of a content of said contents container, comprising:
   a closed sample container with a flexible wall and with an interior,
   a coupling member unconnected to the sample outlet connector and ready for releasable coupling to the sample outlet connector,
   and a communicating passage between the coupling member and the interior of the sample container, at least the interior of the sample container being sterile, and
   comprising a sterility protection device ensuring the sterility of the interior of the sample container in the form of a three-way valve between the coupling member and the sample container, the three-way valve having a connection to the coupling member, a connection to the sample container, and an outlet, and the three-way valve being, before coupling the coupling member to the sample outlet connector, in a closed position in which it bars any access through the three-way valve to the sterile interior of the sample container.

2. A sampling device according to claim 1, wherein the three-way valve is provided with a tamper-evident blocking device.

3. A sampling device according to claim 2, wherein the tamper-evident blocking device comprises a tear-off member preventing the three-way valve from being set to any position other than the closed position.

4. A sampling device according to claim 3, wherein the tear-off member comprises a member, which encapsulates the three-way valve at least partially.

5. A sampling device according to claim 3, wherein the three-way valve comprises a valve housing and a movable valve body and the tear-off member comprises a portion of the valve housing, which portion blocks movement of the valve body.

6. A sampling device according to claim 3, wherein the tear-off member comprises a film member, which encapsulates the three-way valve at least partially.

7. A sampling device according to claim 1, wherein the outlet is provided with an outlet connector.

8. A sampling device according to claim 1, wherein the three-way valve comprises a valve housing and a movable valve body with at least one through passage.

9. A sampling device according to claim 1, comprising a temperature indicator.

10. A sampling device according to claim 1, wherein an additional sterility protection device comprises a sterile packaging encapsulating the sample container, the coupling member and the communicating passage between them.

11. A sampling device according to claim 1, wherein the communicating passage between the coupling member and the interior of the sample container has an internal diameter of at least 4 mm.

12. A sampling device according to claim 1, wherein the coupling member is a socket.

13. A method of obtaining a sample representative of a content of a contents container used in an industrial processing plant by sampling through a sampling valve attached to said contents container and through a sample outlet connector attached to said sampling valve downstream of said sampling valve, said method comprising the steps of:

Step 1): providing a sampling device comprising: a closed sample container with a flexible wall and with an interior; a coupling member for releasable coupling to the sample outlet connector; a communicating passage between the coupling member and the interior of the sample container, at least the interior of the sample container being sterile; a sterility protection device ensuring the sterility of the interior of the sample container in the form of a three-way valve between the coupling member and the sample container, the three-way valve having a connection to the coupling member, a connection to the sample container, and an outlet, said three-way valve being in a closed position in which it bars any access through the three-way valve to the sterile interior of the sample container;

Step 2): subsequently to step 1) coupling said coupling member to the sample outlet connector;

Step 3): subsequently to step 2) directing a cleaning fluid different from the content of the contents container through the sample outlet connector and the coupling member to the three-way valve and out through the outlet of the three-way valve;

Step 4): subsequently to step 3) operating the three-way valve to open the communicating passage between the coupling member and the interior of the sample container;

Step 5): directing the sample of the content of the contents container through the sample outlet connector to the interior of the sample container;

maintaining the coupling member coupled to the sample outlet connector during steps 3), 4), and 5) and during any step intervening between steps 3), 4), and 5), the sampling valve remaining attached to the contents container and the sample outlet connector remaining attached to the sampling valve at least during steps 3), 4), and 5) and during any step intervening between steps 3), 4), and/or 5); and Step 6) disconnecting the coupling member from the sample outlet connector.

14. A sampling device for sampling through a sampling valve attached to a contents container used in an industrial processing plant and through a sample outlet connector attached to said sampling valve downstream of said sampling valve, a sample representative of a content of said contents container, comprising:
   a closed sample container with a flexible wall and with an interior,
   a coupling member unconnected to the sample outlet connector and ready for releasable coupling to the sample outlet connector,
   and a communicating passage between the coupling member and the interior of the sample container, at least the interior of the sample container being sterile, and
   comprising a sterility protection device ensuring the sterility of the interior of the sample container in the form of a three-way valve between the coupling member and the sample container, the three-way valve having a connection to the coupling member, a connection to the sample container, and an outlet, and the three-way valve being, before coupling the coupling member to the sample outlet connector, in a closed position in which it bars any access through the three-way valve to the sterile interior of the sample container, wherein the sampling device is encapsulated in a packaging.

* * * * *